(12) United States Patent
McKenny et al.

(10) Patent No.: US 10,500,058 B2
(45) Date of Patent: Dec. 10, 2019

(54) STAND ALONE INTERBODY FIXATION SYSTEM

(71) Applicant: Alphatec Spine, Inc., Carlsbad, CA (US)

(72) Inventors: Breanna McKenny, Carlsbad, CA (US); Joseph Aferzon, New Britain, CT (US); Jeffrey A. Bash, Middletown, CT (US)

(73) Assignee: Alphatec Spine, Inc., Carlsbad, CA (US)

( * ) Notice: Subject to any disclaimer, the term of this patent is extended or adjusted under 35 U.S.C. 154(b) by 0 days.

(21) Appl. No.: 14/060,424

(22) Filed: Oct. 22, 2013

(65) Prior Publication Data
US 2014/0052260 A1    Feb. 20, 2014

Related U.S. Application Data

(63) Continuation of application No. PCT/US2012/034627, filed on Apr. 23, 2012.

(60) Provisional application No. 61/479,206, filed on Apr. 26, 2011.

(51) Int. Cl.
*A61F 2/44* (2006.01)
*A61F 2/28* (2006.01)
*A61F 2/30* (2006.01)

(52) U.S. Cl.
CPC .............. *A61F 2/442* (2013.01); *A61F 2/447* (2013.01); *A61F 2002/2835* (2013.01); *A61F 2002/3038* (2013.01); *A61F 2002/30289* (2013.01); *A61F 2002/30365* (2013.01); *A61F 2002/30367* (2013.01); *A61F 2002/30382* (2013.01); *A61F 2002/30504* (2013.01); *A61F 2002/30738* (2013.01); *A61F 2002/30787* (2013.01); *A61F 2002/30827* (2013.01);
(Continued)

(58) Field of Classification Search
CPC ........ A61F 2/442; A61F 2/4455; A61F 2/447; A61F 2/446; A61F 2/4465; A61B 17/7064; A61B 17/869
USPC .......................................... 623/17.11, 17.16
See application file for complete search history.

(56) References Cited

U.S. PATENT DOCUMENTS 8,313,528 B1 * 11/2012 Wensel .................... A61F 2/447
                                                                 623/17.11
8,328,872 B2 * 12/2012 Duffield et al. ............ 623/17.16
(Continued)

FOREIGN PATENT DOCUMENTS

WO         98/48738         11/1998
WO      03/055398 A1        7/2003
(Continued)

*Primary Examiner* — Si Ming Ku
(74) *Attorney, Agent, or Firm* — Hoffmann & Baron, LLP (57) ABSTRACT

An interbody spacer system for insertion between a first vertebra and a second vertebra according to the principles of the present disclosure includes and interbody spacer and a first curved blade. The interbody spacer includes an outer wall and a first surface for engaging an endplate of the first vertebra and a second surface for engaging an endplate of the second vertebra. A first entry aperture in the outer wall and a first exit aperture on the first surface communicate with a first curved path extending therebetween. The first curved blade enters the first entry aperture and exits through the first exit aperture to secure the spacer to the first vertebra.

11 Claims, 9 Drawing Sheets

(52) U.S. Cl.
CPC ............. *A61F 2002/30845* (2013.01); *A61F 2002/30919* (2013.01); *A61F 2002/4475* (2013.01)

(56) References Cited

U.S. PATENT DOCUMENTS

| | | | |
|---|---|---|---|
| 8,460,385 B1* | 6/2013 | Wensel | A61B 17/864 623/17.16 |
| 2002/0177898 A1* | 11/2002 | Crozet | 623/17.11 |
| 2005/0143733 A1* | 6/2005 | Petit | 606/60 |
| 2006/0085071 A1* | 4/2006 | Lechmann et al. | 623/17.11 |
| 2006/0136063 A1* | 6/2006 | Zeegers | 623/17.14 |
| 2007/0073404 A1* | 3/2007 | Rashbaum et al. | 623/17.14 |
| 2007/0293948 A1* | 12/2007 | Bagga | A61F 2/4455 623/17.11 |
| 2009/0105832 A1* | 4/2009 | Allain et al. | 623/17.16 |
| 2009/0164020 A1* | 6/2009 | Janowski et al. | 623/17.16 |
| 2009/0265007 A1 | 10/2009 | Colleran | |
| 2010/0145459 A1 | 6/2010 | McDonough et al. | |
| 2010/0256690 A1 | 10/2010 | Appenzeller et al. | |
| 2011/0035007 A1 | 2/2011 | Patel et al. | |
| 2011/0166660 A1* | 7/2011 | Laurence | 623/17.16 |
| 2011/0208311 A1* | 8/2011 | Janowski | 623/17.16 |
| 2011/0230971 A1* | 9/2011 | Donner et al. | 623/17.16 |
| 2012/0271423 A1* | 10/2012 | Wallenstein et al. | 623/17.16 |
| 2013/0150968 A1* | 6/2013 | Dinville et al. | 623/17.16 |
| 2014/0058520 A1 | 2/2014 | Crozet | |

FOREIGN PATENT DOCUMENTS

| | | |
|---|---|---|
| WO | 03/068112 A1 | 8/2003 |
| WO | 2010/028045 A1 | 3/2010 |
| WO | 2010/028056 A1 | 3/2010 |
| WO | 2010/054181 A1 | 5/2010 |
| WO | 2010/121028 A2 | 10/2010 |

* cited by examiner

STAND ALONE INTERBODY FIXATION SYSTEM

CROSS-REFERENCE TO RELATED APPLICATIONS

The present application is a continuation and claims priority under 35 U.S.C. § 120 and § 365(c) to International Application PCT/US2012/034627, filed Apr. 23, 2012, which claims priority to Provisional Application 61/479,206, filed Apr. 26, 2011 and incorporated herein by reference in its entirety.

FIELD

The present disclosure relates generally to spinal fusion devices. More specifically, example embodiments are directed to a stand alone interbody spacer.

BACKGROUND

The background description provided herein is for the purpose of generally presenting the context of the disclosure. Aspects of the description that may not otherwise qualify as prior art at the time of filing, are neither expressly nor impliedly admitted as prior art against the present disclosure.

The spine is a flexible column formed of a plurality of bones called vertebrae. The vertebrae include a hollow cavity and essentially stack one upon the other, forming a strong column for support of the cranium and trunk of the body. The hollow core of the spine houses and protects the nerves of the spinal cord. The different vertebrae are connected to one another by means of articular processes and intervertebral, fibrocartilaginous bodies. Each vertebra includes upper and lower endplates formed from harder compact bone than the softer cancellous bone of the interior of the vertebra.

The intervertebral bodies, also known as intervertebral discs, include a fibrous ring filled with pulpy material. The discs function as spinal shock absorbers and also cooperate with synovial joints to facilitate movement and maintain flexibility of the spine. When one or more discs degenerate through accident or disease, nerves passing near the affected area may be compressed and consequently irritated. The result may be chronic and/or debilitating neck and/or back pain due to these spinal disorders.

Various methods and apparatus have been designed to relieve such back pain, including spinal fusion using an interbody spacer or suitable graft using techniques such as anterior interbody fusion, posterior interbody fusion, or transforaminal interbody fusion surgical techniques. The implants used in-these techniques are placed in the intervertebral disc space between adjacent vertebrae of the spine. Many times an exterior plate and/or screws are used in conjunction with the implant to hold the adjacent vertebrae while the fusion occurs.

Ideally, the interbody spacer should stabilize the intervertebral space and allow fusion of the adjacent vertebrae. Moreover, during the time it takes for fusion to occur, the interbody spacer should have sufficient structural integrity to withstand the stress of maintaining the space without substantially degrading or deforming and have sufficient stability to remain securely in place prior to actual bone ingrowth fusion.

One significant challenge to providing fusion stability (prior to actual bone ingrowth fusion) is preventing spinal extension during patient movement. Distraction of the vertebral space containing the fusion graft may cause the interbody spacer to shift or move disrupting bone ingrowth fusion and causing pain. An exterior plate is often used with the interbody spacer to hold the adjacent vertebrae while the fusion occurs.

The present disclosure provides an interbody spacer capable of holding the adjacent vertebrae steady during fusion without the use of external plates.

SUMMARY

An interbody spacer system for insertion between a first vertebra and a second vertebra according to the principles of the present disclosure includes and interbody spacer and a first curved blade. The interbody spacer includes an outer wall and a first surface for engaging an endplate of the first vertebra and a second surface for engaging an endplate of the second vertebra. A first entry aperture in the outer wall and a first exit aperture on the first surface communicate with a first curved path extending therebetween. The first curved blade enters the first entry aperture and exits through the first exit aperture to secure the spacer to the first vertebra.

In other features, a second entry aperture in the outer wall and a second exit aperture on the second surface communicate with a second curved path therebetween. A second curved blade enters the second entry aperture and exits through the second exit aperture to secure the spacer to the second vertebra.

In still other features, the first curved path includes one of a helical path, a spiral path, and a corkscrew path. The outer wall forms an annular shape including a hollow cavity. The first surface includes a plurality of projections for engaging the first endplate and providing a path for material flow. An anterior side of the outer wall includes a recessed portion for receiving the first curved blade. The outer wall includes an anterior wall, a posterior wall, and a pair of side walls that form a substantially trapezoidal shape.

In yet other features, the first curved blade includes a base with an attachment feature and a self-tapping start for piecing the first endplate. The first curved blade advances through the interbody spacer and the first endplate along at least one of a helical, spiral, and corkscrew path. The first curved blade includes a tip at a distal end configured to enter an outer side of the first endplate at a first location and project towards an inner side of the first endplate at a second location. The first curved blade includes a tip at a distal end configured to pierce the first endplate at a first location upon entering the first vertebra and pierce the first endplate at a second location upon exiting from the first vertebra.

An interbody spacer system includes a cage including an anterior wall and a posterior wall connected by a pair of side walls, the anterior wall having a first entry aperture and a first of the side walls having a first exit aperture, and a first helical blade that enters the cage through the first entry aperture and exits through the first exit aperture to rigidly secure the cage to a first vertebra.

In other features, the system includes a first helical path between the first entry aperture and the first exit aperture configured to slidably receive the first helical blade. The first entry aperture is disposed on an outer face of the anterior wall facing away from a spine surrounded by the first vertebra. The first exit aperture is disposed on at least one of an upper surface and a lower surface of the side wall. The anterior wall includes a second entry aperture.

In other features, a second of the side walls includes a second exit aperture. A second helical blade enters the cage through the second entry aperture and exits through the second exit aperture to rigidly secure the cage to a second vertebra.

DETAILED DESCRIPTION

The following description is merely exemplary in nature and is in no way intended to limit the disclosure, its application, or uses. For purposes of clarity, the same reference numbers will be used in the drawings to identify similar elements. As used herein, the phrase at least one of A, B, and C should be construed to mean a logical (A or B or C), using a non-exclusive logical "or." It should be understood that steps within a method may be executed in different order without altering the principles of the present disclosure.

Embodiments of the invention will now be described with reference to the Figures, wherein like numerals reflect like elements throughout. Embodiments of the invention may include several novel features, no single one of which is solely responsible for its desirable attributes or which is essential to practicing the invention described herein. The words proximal and distal are applied herein to denote specific ends of components of the instrument described herein. For example only, a proximal end refers to the end of an instrument nearer to an operator of the instrument when the instrument is being used. A distal end refers to the end of a component further from the operator and extending towards the surgical area of a patient and/or the implant. Similarly, the words left and right, top and bottom, and upper and lower may denote opposite sides of a component.

Accordingly, a stand alone interbody spacer system according to the principles of the present disclosure includes a pre-assembled multi-component design which integrates a fixation feature with an interbody spacer with no additional support required. In preferred embodiments, the system 100 is used in spinal fusion surgeries including, but not limited to anterior interbody fusion, posterior interbody fusion, or transforaminal interbody fusion, lateral and cervical procedures, wherein two or more vertebrae are joined or fused together for the treatment of spinal disorders such as spondylolisthesis, scoliosis, severe disc degeneration, or spinal fractures. While the embodiments are described primarily in the context of an anterior cervical procedure, use with other procedures are also contemplated. The system 100 may be used in a variety of spinal procedures, including open procedures and minimally invasive surgery (MIS) procedures using low profile instrumentation which facilitates a less invasive approach through a smaller incision. As can be understood by one skilled in the art, these embodiments are shown for illustrative purposes and are not intended to limit the scope of the invention.

The unique design of the stand alone interbody fixation system 100 provides solid fixation in all aspects (flexion, extension, torsion, rotation, migration). In many embodiments, the system 100 is configured to use a single instrument to distract, insert, and deploy the system 100. The design allows for multiple footprint shapes, ranging from 10-20 mm in both length and width to ensure adequate contact with cortical rim. In many embodiments, the design includes a tapered leading portion that allows smooth insertion and deployment. The height may range from 8-20 mm, but other heights are also contemplated, depending on location with lordosis ranging from 0-20 degrees to accommodate surgical needs.

Portions of the system 100 may comprise a material, such as a thermoplastic, a polymer, or a composite thereof, that is sufficiently resilient to withstand stress or pressure of bodily movement and positioning, while providing a degree of elasticity and also providing biostablity and biocompatibility. The material should have a modulus of elasticity that is comparable to bone. For example, some portions may be made of polyether ether ketone (PEEK), a thermoplastic with a Young's modulus of elasticity of about 3.6 GPa and a tensile strength of about 90 MPa. Also, because PEEK is resistant to both organic and aqueous environments, it is practical for the minimally invasive lateral intervertebral fixation device. Other materials that may be used include metals, ceramics, medical plastics, coral, and other medically applicable materials.

Referring now to FIGS. 1-7C, an exemplary stand alone interbody fixation system 100 for spinal fusion surgeries includes a cage 102 and one or more curved blades 104 or curved spikes. The curved blades 104 may include a three-dimensional curvature such as a helical, spiral or corkscrew shape. The system 100 may be inserted into the intervertebral space between adjacent vertebrae to provide support in place of damaged intervertebral discs. The cage 102 and curved blades 104 engage with vertebrae above and below the cage 102. The system 100 may be inserted into the intervertebral space using a tool (not shown) that maintains the curved blades 104 in proximity to the cage 102. For example, the tool may include one or more features that engage and support the cage 102 during insertion. Additional features may maintain the curved blades 104 within close proximity to the cage 102. Thus, the system 100 may be inserted into the intervertebral space in one step before the curved blades 104 are deployed to secure the cage 102 between the adjacent vertebrae. The tool may further include features that engage and rotate the curved blades 104. While rotating, the curved blades 104 enter the cage 102 at one location and exit the cage 102 from another location. The curved blades 104 deploy to engage with the vertebrae above and below the cage 102.

Figure 1:
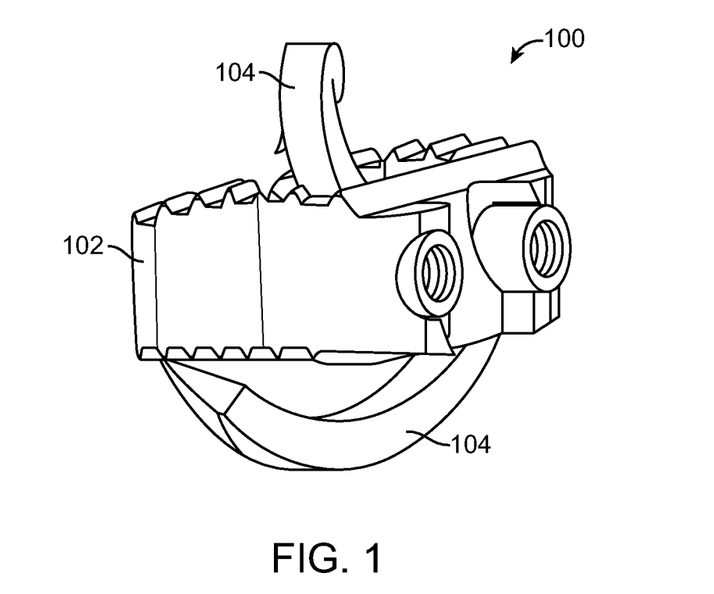
FIGS. 1 and 2 are perspective views of an exemplary stand alone interbody spacer according to the principles of the present disclosure.
Figure 2:
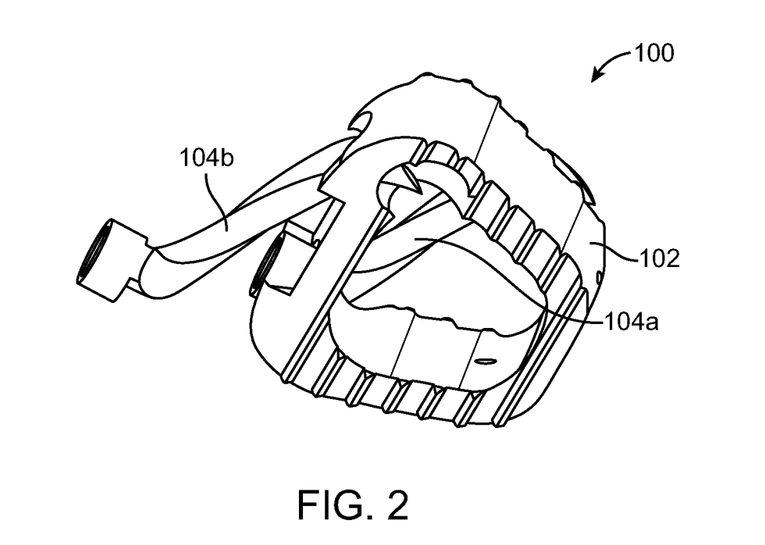
Figure 3A:
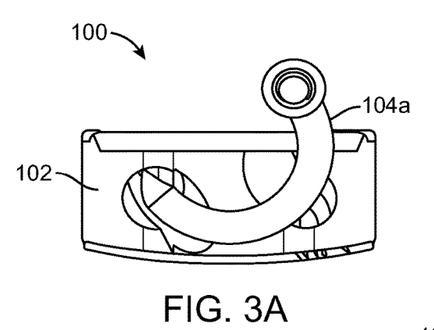
FIGS. 3A-3D are perspective views of the stand alone interbody spacer in a non-deployed position according to the principles of the present disclosure.
Figure 3B:
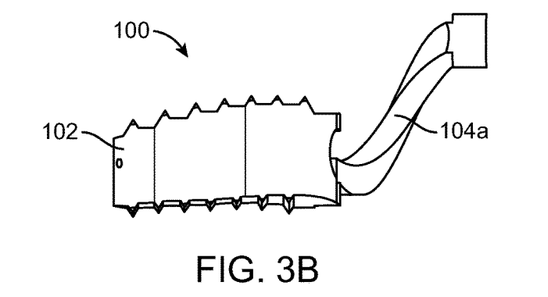
Figures 3C, 3D:
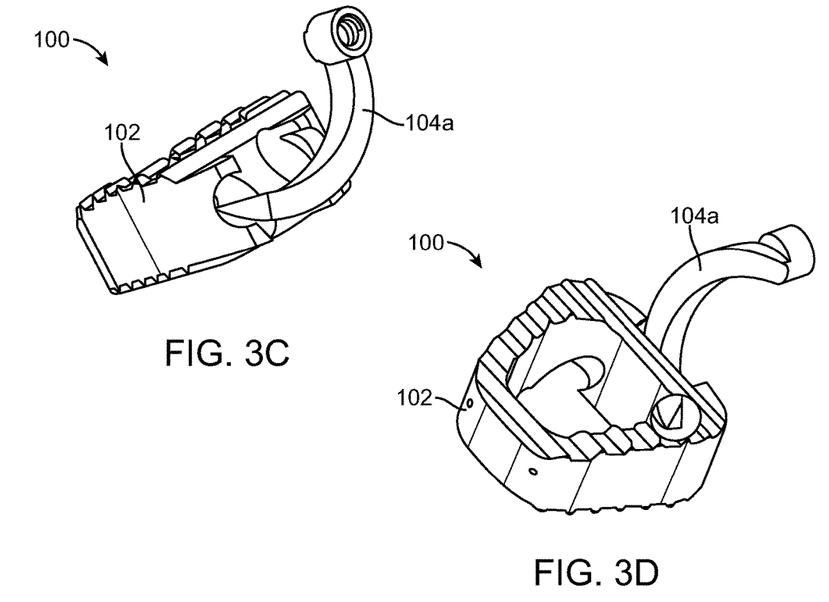
Figure 4A:
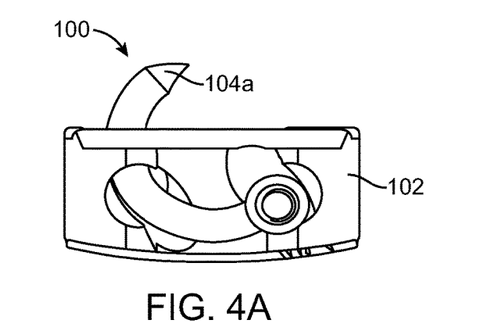
FIGS. 4A-4D are perspective views of the stand alone interbody spacer in a partially deployed position according to the principles of the present disclosure.
Figure 4B:
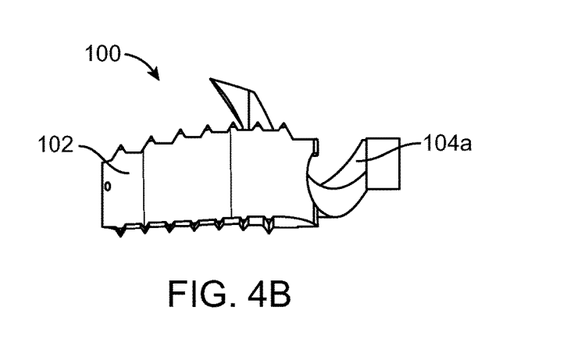
Figure 4C:
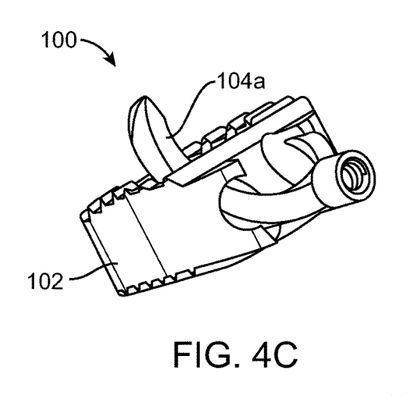
Figure 4D:
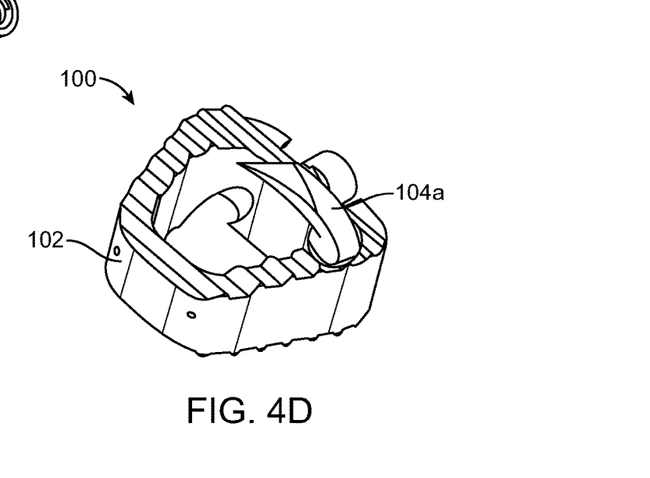

FIGS. 1 and 2 illustrate a two blade configuration of the stand alone interbody fixation system 100. In FIG. 1, both curved blades 104 are shown fully deployed to engage with vertebrae (not shown) both above and below the cage 102. In FIG. 2, a first curved blade 104*a* is shown in a deployed position while a second curved blade 104*b* is shown in a non-deployed position. Thus, each of the curved blades 104 may be deployed individually. In other examples, the curved blades 104 may be deployed simultaneously. For example, the tool may include features that enable singular or simultaneous deployment of the curved blades 104. FIGS. 3A-5D illustrate actuation or deployment of the first curved blade 104*a* with respect to the cage 102. FIGS. 6A-7C illustrate actuation or deployment of the second curved blade 104*b* with respect to the cage 102 and the first curved blade 104*a*.

FIGS. 8-12 illustrate additional features of the cage 102 that enable insertion and fixation between the adjacent vertebrae. The cage 102 may be made of a rigid construction and preferably provided in several different sizes and shapes to fill differently sized evacuated spaces in differently sized individuals. The cage 102 may be constructed of a radiolucent material, such as polyether ether ketone (PEEK), commercially pure titanium, a titanium alloy, or any other biologically acceptable inert materials that would provide the cage with a rigid structure.

The cage 102 may be annular in configuration and include an anterior wall 106, side walls 108, 110, and a posterior wall 112. The anterior wall 106 and posterior wall 112 lie in planes running substantially parallel to the coronal plane of the patient with the anterior wall 106 facing away from the spinal cord and the posterior wall 112 facing towards the spinal cord. The width W1 of the anterior wall 106 may be greater than the width W2 of the posterior wall forming a substantially trapezoidal geometry when viewed from above as in FIG. 12. The trapezoidal geometry may correspond to the geometry of the cervical vertebrae. The cage 102 may include substantially uniform thickness T throughout the various walls which form a hollow cavity 114. Alternatively, each wall may include varying thickness. Similarly, the cage 102 may include substantially uniform height H throughout the various walls. Alternatively, the height H of the cage 102 may decrease from the anterior wall 106 to the posterior wall 112 forming a wedge-shaped geometry that closely matches geometry typically associated with the cervical curvature of the spine.

The cage 102 further includes an upper surface 116 and a lower surface 118 that engage with the adjacent vertebrae. The upper surface 116 generally faces towards the head of the patient while the lower surface 118 generally faces away from the head. In some embodiments, a plurality of outwardly projecting sharp projections 120 such as raised ridges/teeth/striations are formed on the surfaces 116, 118 for biting into and gripping the vertebral end plates (not shown). The projections 120 may have a variable thickness, height, and width as well as an angle with respect to the surfaces 116, 118. The projections 120 may be disposed at slightly offset angles with respect to each other or, alternatively with respect to the ridges on different portions of the cage, to reduce the possibility of the ridges sliding in any direction along the end plates and to prevent rotation of the cage on the end plate. While it may be preferable that the projections 120 are identical in configuration on the upper and lower surfaces, in some embodiments, the ridges or teeth may have a different pattern for each surface. The projections 120 may also provide flow paths as bone cement and material are later added to the fusion.

Various attachment features may be included to couple the cage 102 with an insertion and/or deployment tool. Although the present example does not illustrate attachment features, one skilled in the art can readily appreciate that various indentations, tabs, and the like may be added to the outer surface of the anterior wall 106, side walls 108, 110, and/or posterior wall 112 to facilitate engagement with such devices. For example, openings may be spaced about the cage 102 and configured to receive or engage an insertion tool or blade activation tool (not shown), or used to pack bone or other suitable bone graft material.

Figure 5A:
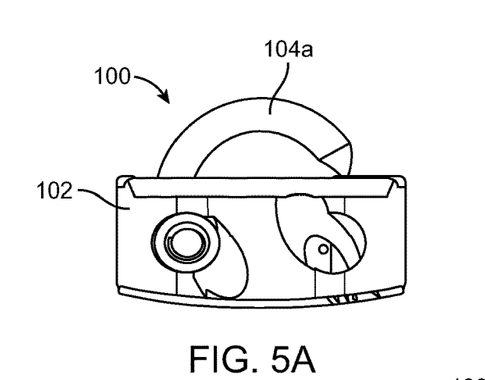
FIGS. 5A-5D are perspective views of the stand alone interbody spacer in fully deployed position according to the principles of the present disclosure.
Figure 5B:
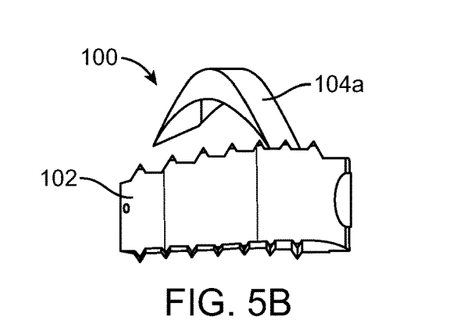
Figure 5C:
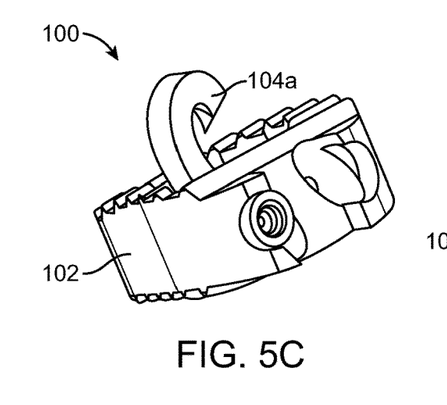
Figure 5D:
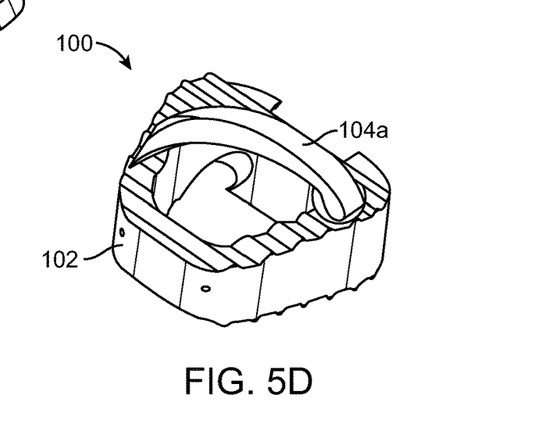
Figure 6A:
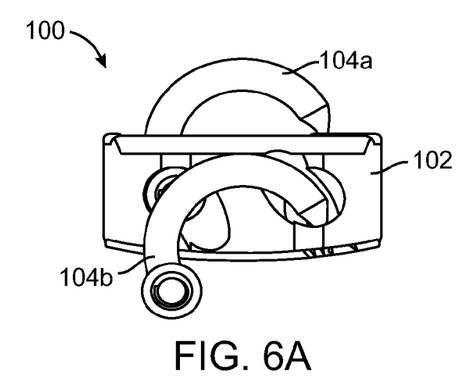
FIGS. 6A-6C are a series of anterior elevational views of the stand alone interbody spacer as a second blade deploys according to the principles of the present disclosure.
Figure 6B:
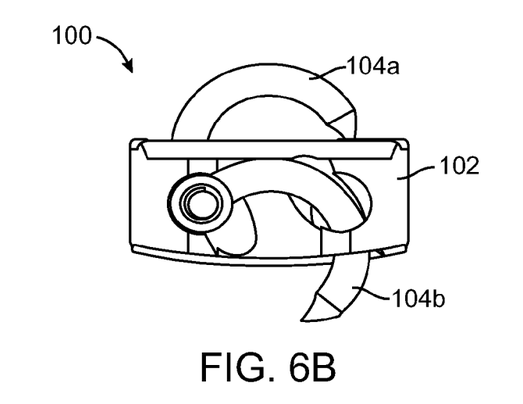
Figure 6C:
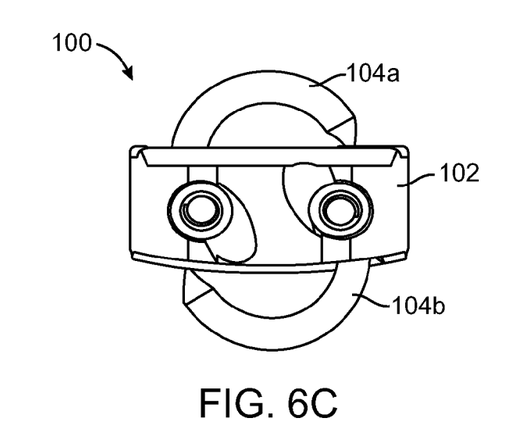
Figure 7A:
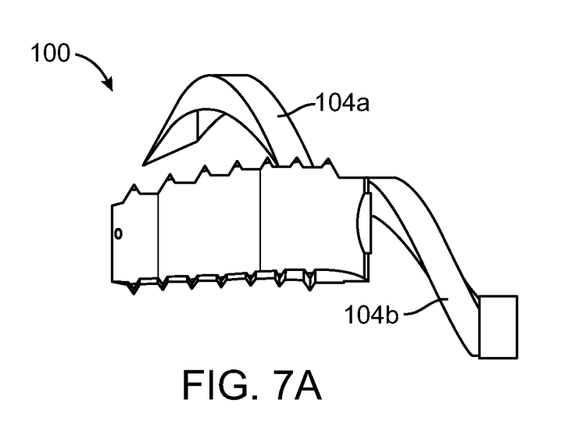
FIGS. 7A-7C are a series of anterior elevational views of the stand alone interbody spacer as the second blade deploys according to the principles of the present disclosure.
Figure 7B:
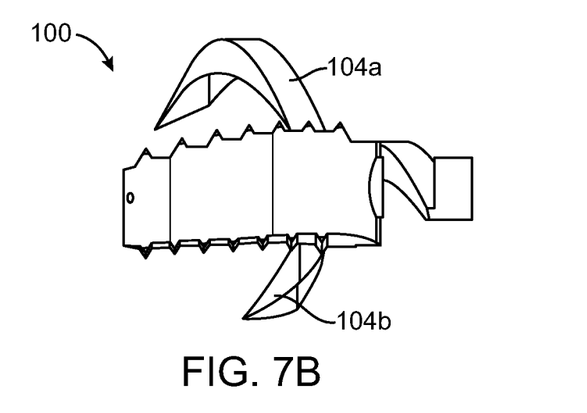
Figure 7C:
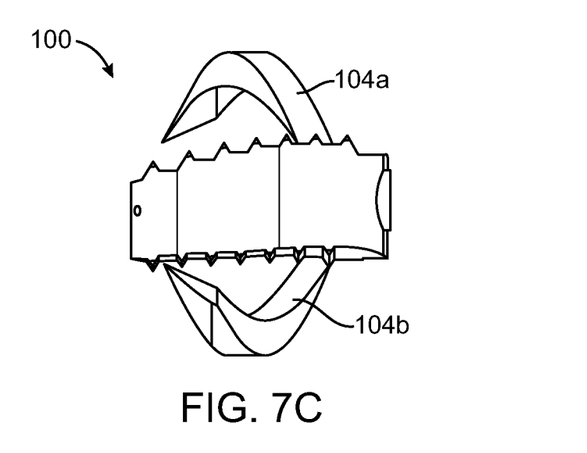
Figure 8:
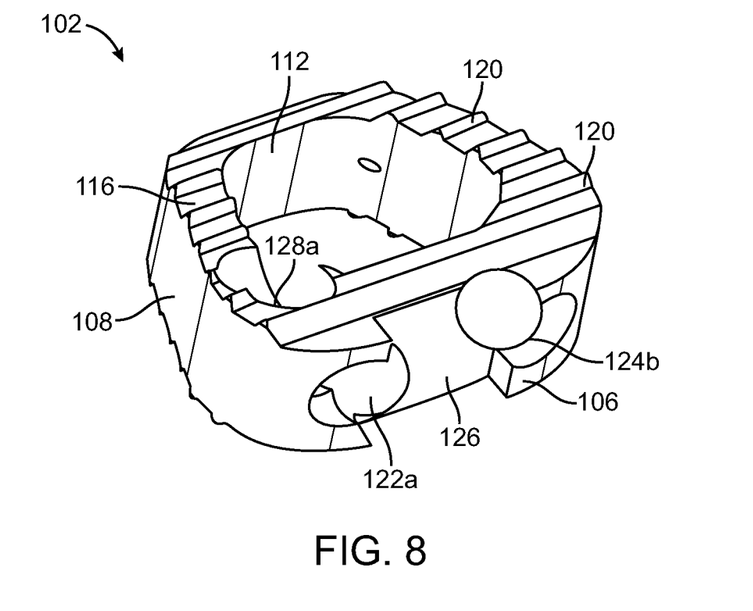
FIGS. 8-12 are various views of a cage of the stand alone interbody spacer according to the principles of the present disclosure.
Figure 9:
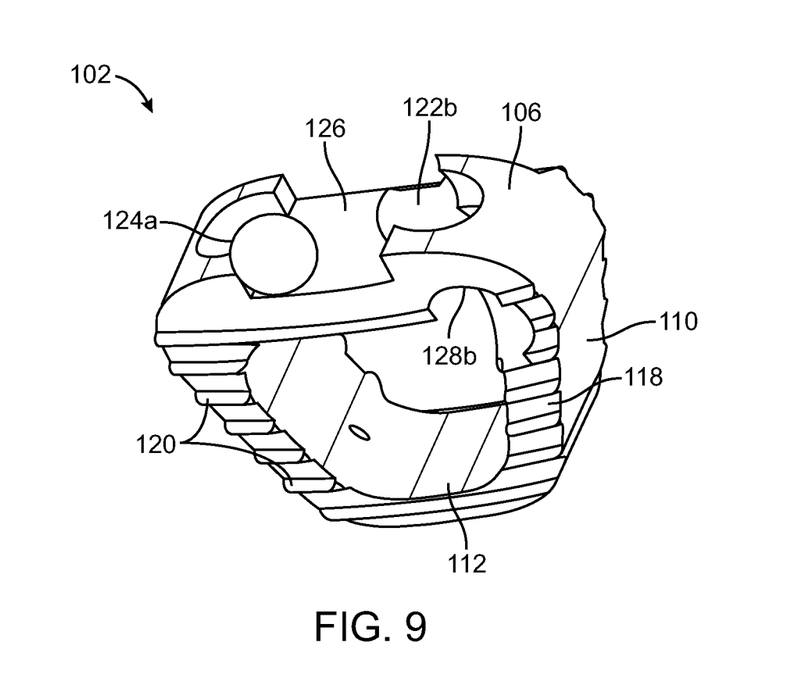
Figure 10:
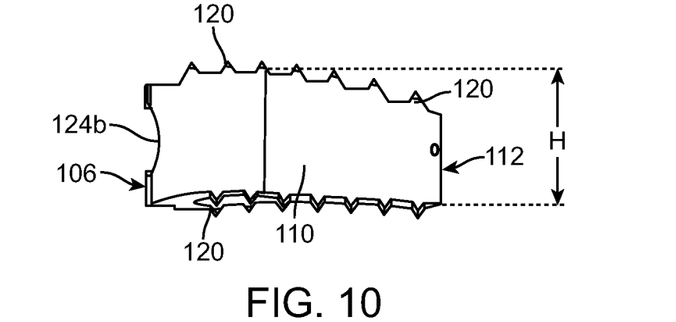
Figure 11:
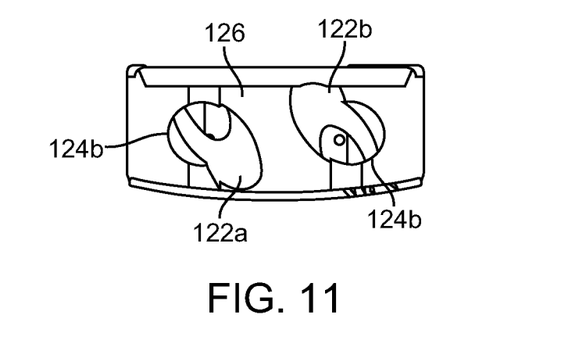
Figure 12:
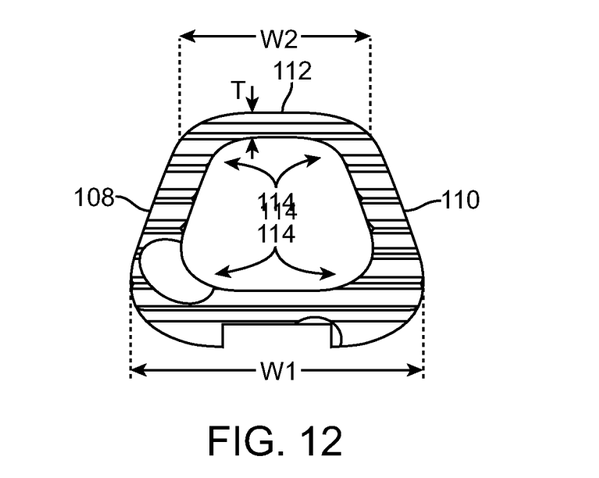

The cage 102 includes an upper blade passage 122*a* and a lower blade passage 122*b* (collectively blade passages 122) for receiving an upper curved blade 104*a* and a lower curved blade 104*b* respectively. On the outer surface of the anterior wall 106, entry apertures 124*a*, 124*b* (collectively 124) may be formed to receive the curved blades 104. The entry apertures 124 may be disposed on a recessed portion 126 of the anterior wall 106 to enable the curved blades 104 to lie flush with the outer surface of the anterior wall 106 upon full deployment as illustrated in FIGS. 5B and 7C. Each entry aperture 124 opens to a corresponding one of the blade passages 122. The blade passages 122 open to corresponding exit apertures 128*a*, 128*b* (collectively 128) on the upper surface 116 and lower surface 118 of the cage 102. For example, the exit apertures 128 may be disposed on the side walls 108, 110.

Figure 16:
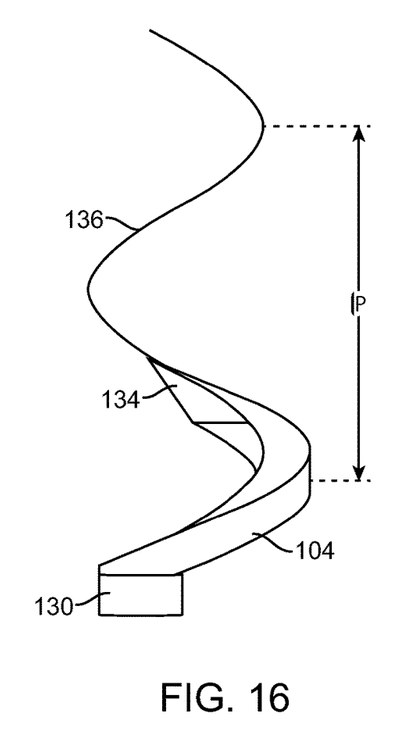
FIG. 16 illustrates a curved path traveled by the exemplary blade according to the principles of the present disclosure.

The blade passages 122 include geometric features for receiving the curved blades 104 as shown in FIGS. 1-7C. The blade passages 122 form curved paths corresponding to the curved path followed by the curved blades 104 as shown in FIG. 16. The upper blade passage 122*a* follows a curved path of substantially uniform cross-section from the entry aperture 124*a* to the exit aperture 128*a* on the upper surface 116. The lower blade passage 122*b* follows a curved path of substantially uniform cross-section from the entry aperture 124*b* to the exit aperture 128*b* on the lower surface 118. Each of the blade passages 122 may extend through a portion of the anterior wall 106 and portions of the side walls 108, 110 before exiting on the upper surface 116 and lower surface 118 of the cage 102. Thus, each curved blade 104*a* and 104*b* enters the cage 102 through the anterior wall 106 and exits through the upper surface 116 and lower surface 118 of the cage 102 respectively.

The apertures 124, 128 and/or blade passages 122 may include blade resistance/locking features (not shown) to hold the blades in one or more positions. These features may include grooves, notches or dimples that couple or interact with ridges, tabs or bumps on the blades. For example, when the curved blade 104*a* is inserted into entry aperture 124*a*, bumps may interact with one of the grooves. As the blade is rotated, the bumps may move from one set of grooves in a non-deployed position to another set of grooves in the deployed position, to form a locking mechanism. Other openings (not shown) may be generally rectangular in shape to accommodate an insertion tool or blade activation tool having a center blade activation portion disposed between a pair of prongs, so that the tool can grip the openings of the cage 102 and/or rotate the blades 104. A blade stopping feature (not shown) may also be used to contact the blades 104 and prevent the blades 104 from rotating more then a desired angle.

Figure 13:
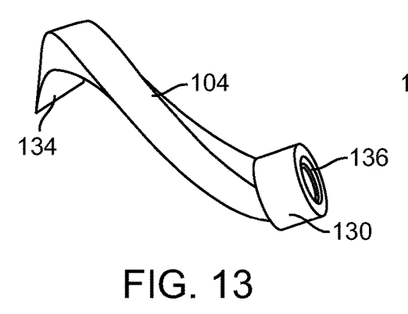
FIGS. 13-15 are various views of an exemplary blade of the stand alone interbody spacer according to the principles of the present disclosure.
Figure 14:
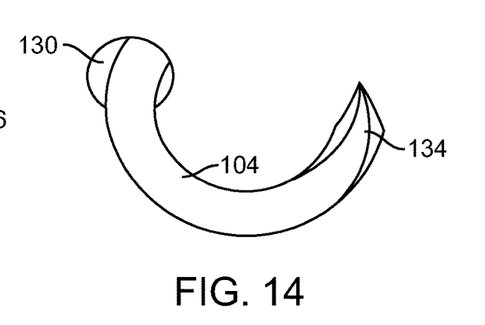
Figure 15:
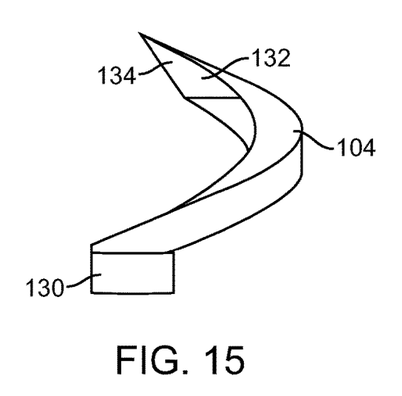

FIGS. 13-15 depict various views of an exemplary curved blade 104. The curved blade 104 includes a base 130 which may include, for example a short shaft having an axis of rotation, at a proximal end and a tip 132 at a distal end. The tip 132 may include a self-tapping start 134 that enables the curved blade 104 to cut into the endplate of the vertebra without a pilot or starter hole. The base 130 may include various attachment features to enable coupling of the curved blade 104 to the insertion tool or removal tool (not shown). For example, the base 130 may include an internal thread 136 to enable a driving feature of the insertion tool to drive the curved blade 104. The curved blade 104 may include a substantially uniform cross-sectional area. Alternatively, the curved blade 104 may include an increasing cross-sectional area from the tip 132 to the base 130. As the curved blade 104 advances through the endplate of the vertebra, the increase in the dimensions may provide a tighter fit within the vertebra.

Referring now to FIG. 16, each of the curved blades 104 travels along a curved path 136 when deployed from or inserted into the cage 102. The curved path 136 maximizes bone purchase and allows the curved blades 104 to engage with the endplates of the vertebrae at multiple points. For example, the start 134 of the first curved blade 104*a* may pierce the endplate of an upper vertebra at one location, travel within the softer interior of the upper vertebra, and exit the endplate in another location along the curved path. Thus, the first curved blade 104*a* anchors to the upper vertebra at two locations with a portion of the first curved blade 104*a* inside the upper vertebra between the two locations. Similarly, the start 134 of the second curved blade 104*b* may pierce the endplate of an adjacent lower vertebra at one location, travel within the softer interior of the lower vertebra, and exit the endplate at another location along the curved path. Thus, the second curved blade 104*b* anchors to the lower vertebra at two locations with a portion of the second curved blade 104*b* inside the lower vertebra between the two locations. Furthermore, the curved blades 104 may include a thread pitch P and that enables full deployment and insertion into the vertebra with a single rotation of the base 130.

Thus, the curved blades 104 may anchor to the harder compact bone of the endplates in more than one location. In contrast, a screw according to the prior art may only pass through the harder bone at one location. If the thread on the screw breaks loose from the cancellous material or if the harder bone at the entry point for the screw becomes fractured, the screw will no longer provide rigid fixation. For a curved blade to suffer a similar failure, the blade would have to back out completely from two anchor points in the harder bone of the endplate.

Example embodiments of the methods and systems of the present invention have been described herein. As noted elsewhere, these example embodiments have been described for illustrative purposes only, and are not limiting. Other embodiments are possible and are covered by the invention. Such embodiments will be apparent to persons skilled in the relevant art(s) based on the teachings contained herein. Thus, the breadth and scope of the present invention should not be limited by any of the above-described exemplary embodiments but should be defined only in accordance with the following claims and their equivalents. The broad teachings of the disclosure can be implemented in a variety of forms. Therefore, while this disclosure includes particular examples, the true scope of the disclosure should not be so limited since other modifications will become apparent to the skilled practitioner upon a study of the drawings, the specification, and the following claims.

The invention claimed is:

1. An interbody spacer system for insertion between a first vertebra and a second vertebra, the interbody spacer system comprising:

an interbody spacer having an outer wall, a first surface, and a second surface, the first surface configured to engage a first endplate of the first vertebra, the second surface configured to engage a second endplate of the second vertebra;

a first entry aperture in the outer wall and a first exit aperture on the first surface;

a first helical passageway defining only a first helical path, the first helical passageway in communication with the first entry aperture and the first exit aperture; and a first blade that includes a first base and a first helical body that extends from the first base to a first distal tip, wherein the first helical body is configured to enter the first entry aperture, extend along the first helical path through the first helical passageway, and exit through the first exit aperture, wherein upon rotation of the first base the first helical body is configured to enter the first endplate through a first location in the first endplate and exit the first endplate through a second location in the first endplate such that a portion of the first helical body is disposed inside the first vertebra between the first location and the second location and the first distal tip extends generally toward the first surface, wherein the first blade is configured to anchor the spacer to the first vertebra at the first location and the second location.

2. The system of claim 1, further comprising a second entry aperture in the outer wall and a second exit aperture on the second surface.

3. The system of claim 2, further comprising a second helical passageway defining only a second helical path, the second helical passageway in communication with the second entry aperture and the second exit aperture.

4. The system of claim 3, further comprising a second blade that includes a second base and second helical body that extends from the second base to a second distal tip, the second helical body is configured to enter the second entry aperture, extend in along the second helical path through the second helical passageway, and exit through the second exit aperture, wherein upon rotation of the second base the second helical body is configured to enter the second endplate through a third location of the second endplate and exit the second endplate through a fourth location in the second endplate such that a portion of the second helical body is disposed inside the second vertebra between the third location and the fourth location and the second distal tip extends generally toward the second surface, wherein the second curved blade is configured to anchor the spacer to the second vertebra at the third location and the fourth location.

5. The system of claim 1, wherein the outer wall forms an annular shape including a hollow cavity.

6. The system of claim 1, wherein the first surface includes a plurality of projections to engage the first endplate to provide a path for material flow.

7. The system of claim 1, wherein an anterior side of the outer wall includes a recessed portion to receive the first base of the first blade.

8. The system of claim 1, wherein the first base of the first blade includes an attachment feature and the distal tip of the first blade includes a self-tapping start to pierce the first endplate.

9. The system of claim 1, wherein the first blade advances through the interbody spacer and the first endplate along the first helical passageway, wherein the first blade extends inside the first vertebra between the first location and the second location.

10. The system of claim 1, wherein the first distal tip is configured to enter the first endplate through the first location and exit through the second location of the first endplate.

11. The system of claim 1, wherein the outer wall comprises an anterior wall, a posterior wall, and a pair of sidewalls that form a substantially trapezoidal shape.

* * * * *